United States Patent [19]

Meier et al.

[11] Patent Number: 5,278,341

[45] Date of Patent: Jan. 11, 1994

[54] N-ACYLAMINOALKYL 2-HYDROXYETHYL SULFIDES AND A PROCESS FOR THEIR PREPARATION

[75] Inventors: Michael Meier; Heinrich Angenendt, both of Frankfurt am Main; Peter Mischke, Bad Soden am Taunus, all of Fed. Rep. of Germany

[73] Assignee: Hoechst Aktiengesellschaft, Gebaeude, Fed. Rep. of Germany

[21] Appl. No.: 923,956

[22] PCT Filed: Feb. 27, 1991

[86] PCT No.: PCT/EP91/00360

§ 371 Date: Sep. 4, 1992

§ 102(e) Date: Sep. 4, 1992

[87] PCT Pub. No.: WO91/13867

PCT Pub. Date: Sep. 19, 1991

[30] Foreign Application Priority Data

Mar. 7, 1990 [DE] Fed. Rep. of Germany ....... 4007048

[51] Int. Cl.$^5$ ............................................. C07C 235/08
[52] U.S. Cl. .................................... 564/224; 564/215; 564/500; 564/501
[58] Field of Search ....................... 564/215, 224, 500; 560/253; 558/29

[56] References Cited

U.S. PATENT DOCUMENTS

3,278,526 10/1966 Louthan et al. .................. 504/209

OTHER PUBLICATIONS

Kandror et al, Selective Inhibition of the Radical Addition of Thiols to Olefins..., CA 77 (23): 151194g, 1972.

*Primary Examiner*—Glennon H. Hollrah
*Assistant Examiner*—Deborah Lambkin
*Attorney, Agent, or Firm*—Connolly and Hutz

[57] ABSTRACT

The invention relates to N-acyl-aminoalkyl-2-hydroxyethylsulfides of formula $R-CONH-(CH_2)_n-S-CH_2-CH_2-OH$, where R is a hydrogen atom or a ($C_1$-$C_4$) alkyl group and n is an integer between 3 and 6, and to a method for preparing them. The method consists in reacting compounds of formula $R-CONH-(CH_2)_m-CH=CH_2$, where R has the above-mentioned meaning and m is an integer between 1 and 4, with the equivalent quantity of mercaptoethanol at approximately 15° to approximately 150° C. in the presence of a radical starter and in the presence or in the absence of a solvent which is inert to the reactants and to radical reactions.

5 Claims, No Drawings

N-ACYLAMINOALKYL 2-HYDROXYETHYL SULFIDES AND A PROCESS FOR THEIR PREPARATION

DESCRIPTION

The invention relates to N-acylaminoalkyl 2-hydroxyethyl sulfides of the formula (A)

$$R\text{---CONH---}(CH_2)_n\text{---S---}CH_2\text{---}CH_2\text{---OH} \quad (A),$$

in which R is a hydrogen atom or an alkyl($C_1$–$C_4$) radical and n is an integer from 3 to 6, and to a process for their preparation by reaction of compounds of the formula (B)

$$R\text{---CONH---}(CH_2)_m\text{---}CH=CH_2 \quad (B),$$

in which R is as defined above and m is an integer from 1 to 4, with mercaptoethanol in the presence of a free-radical initiator.

The N-acylaminoalkyl 2-hydroxyethyl sulfides according to the invention are precursors for the preparation of aminoalkyl ethyl sulfones of the formula (C)

$$H_2N\text{---}(CH_2)_n\text{---}SO_2\text{---}CH_2\text{---}CH_2\text{---}X \quad (C),$$

in which n is as defined above and X is an inorganic or organic radical, preferably a group or an element from the series comprising —OH, —$OSO_3H$, —Cl or —O-$COCH_3$, which in turn serve as components for the preparation of reactive dyes (DE 2,040,620 or EP 0,141,776).

Hitherto it has been possible to obtain the compounds of the formula (C) as mentioned by oxidation of the non-acylated aminoalkyl sulfides of the general formula (D)

$$H_2N\text{---}(CH_2)_n\text{---}S\text{---}CH_2\text{---}CH_2\text{---}X \quad (D),$$

in which n and X are as defined above.

Several processes for preparing the sulfides of the abovementioned formula (D) are already known. Thus, according to J. Med. Chem. 9, 217 (1966), 3-aminopropyl 2-hydroxyethyl sulfide is obtained by reaction of mercaptoethanol with 3-bromoaminopropane hydrobromide. However, the disadvantage of this method is the formation of 2 equivalents of sodium bromide. An improved process for the preparation of this sulfide operating without the formation of salt is described in DE 2,040,620: allylamine is reacted with mercaptoethanol at 50°–150° C. with the addition of azoisobutronitrile (AIBN). No yields are given in this publication. Upon repeating this process (see Example 9 below), yields of only 56.6% of theory were obtained. Thus, it may be stated that this preparation process does not meet the demands of an industrial process either.

A modification of this preparation process is described by the reaction of 4-nitro-N-allylbenzamide at 120°–140° C. with mercaptoethanol, also with the addition of free-radical formers (DE 2,040,620, Example 1). In this case, too, no yields are given. Repetition of this reaction (see Example 11 below) gave a crude yield of 78.3% of theory. However, this modified process is no economically feasible route for preparing 3-aminopropyl 2-hydroxyethyl sulfide, due to the formation of 3-nitrobenzoic acid.

U.S. Pat. No. 3,278,526 describes the reaction of N-alkenylamides with hydrogen sulfide and thiols with the addition of free-radical initiators, in which the maximum yields of 66% are unsatisfactory. Japanese Patent 44/10,770 also teaches that in the reaction of N-acylalkenylamides with mercaptans the addition of special free-radical initiators is necessary. The yields of these reactions are 57–91% of theory.

For the reasons mentioned above, there was a need for an economical and technically feasible process for the preparation of N-acylaminoalkyl 2-hydroxyethyl sulfides.

It has now been found that N-acylaminoalkyl 2-hydroxyethyl sulfides of the formula (1)

$$R\text{---CONH---}(CH_2)_n\text{---S---}CH_2\text{---}CH_2\text{---OH} \quad (1)$$

in which R is a hydrogen atom or an unbranched or branched alkyl($C_1$–$C_4$) radical and n is an integer of from 3 to 6 can be prepared in high yields and in high purity by reacting compounds of the general formula (2)

$$R\text{---CONH---}(CH_2)_m\text{---}CH=CH_2 \quad (2)$$

in which R is as defined above and m is an integer from 1 to 4 with the equivalent amount of mercaptoethanol at temperatures of about 15° to about 150° C., preferably of about 20° to about 100° C., particularly preferably of about 25° to about 80° C., in the presence of a free-radical initiator in the presence or in the absence of a solvent which is inert towards the reactants and towards free-radical reactions.

Oxygen preferably serves as the free-radical former. It can be introduced into the reaction mixture, for example, in pure form or as a mixture with an inert gas or inert gas mixture, preferably in the form of air.

According to the process, the procedure is either such that both reactants are mixed and brought to the reaction temperature in the presence of air and/or oxygen, or such that one of the two reactants is initially introduced and the second reactant is metered in within the temperature ranges mentioned. It is in principle immaterial whether the compound of the formula (2) mentioned is initially introduced and the mercaptoethanol is metered in or whether the procedure is the other way round.

The inert solvent used for the reaction can be an aromatic hydrocarbon which may be halogenated or a paraffin or paraffin mixture or a halogenated aliphatic hydrocarbon which is liquid at the reaction temperature used in each case, such as, for example, benzene, monochlorobenzene, 1,2-, 1,3- or 1,4-dichlorobenzene, trichlorobenzene, carbon tetrachloride or a paraffin having at least 6 carbon atoms.

The reaction can be carried out at atmospheric pressure or superatmospheric pressure. However, it is preferred to work at atmospheric pressure.

Examples of suitable starting compounds of the formula (2) mentioned are N-allylacetamide, N-allylformamide, N-allylpropionamide, N-allylvaleramide, N-3-butenylformamide, N-3-butenylacetamide, N-4-pentenylformamide, N-4-pentenylacetamide, N-5-hexenylformamide and N-5-hexenylacetamide.

As already mentioned, it is advantageous and most favorable to react both reaction components in equivalent amounts. However, it is also possible to use either of the reaction components in excess or in a less than equivalent amount with respect to the other component. However, such a procedure cannot be considered advantageous, since that component used in excess must subsequently be removed by distillation.

It must be considered surprising that the compounds of the formula (1) mentioned are formed in high yields and in high purity from the compound of the formula (2) mentioned and mercaptoethanol even at room temperature and this reaction, in contrast to the prior art (see Comparative Example 7), can be initiated by introducing only oxygen and, in a particularly simple embodiment, by introducing air, i.e. without using special free-radical initiators, such as, for example, azoisobutyronitrile.

The compounds of the formula (1) mentioned obtainable according to the invention can be converted directly by oxidation to the corresponding sulfone or by deacylation to the amines of the formula (2) mentioned at the beginning, which, in turn, are used as precursors for the preparation of reactive dyes.

The examples which follow serve to illustrate the present invention without limiting it thereto.

EXAMPLE 1

N-acetyl-3-aminopropyl 2-hydroxyethyl sulfide

A mixture of 99.1 g (1.0 mol) of N-allylacetamide and 78.1 g (1.0 mol) of mercaptoethanol are vigorously stirred at 25° C. with the addition of air. After 8 hours, the reaction is complete (GC). 177.1 g of N-acetyl-3-aminopropyl 2-hydroxyethyl sulfide are formed as a yellowish oil having a purity by GC of 94.3%, which corresponds to a yield of 94.2% of theory.

$^1$H-NMR (CDCl$_3$): δ=1.50–1.95 (m;2H;CH$_2$CHhd 2CH$_2$), 1.95 (s;3H;COCH$_3$), 2.55, 2.62 (t, J=7Hz;$\overline{4H}$;2 —CH$_2$S), 3.25 (pseudo q, J=7Hz;2H;CH$_2$NH), 3.70 (t, J=7Hz;2H;CH$_2$OH), 4.3 (s;1H;OH), 7.1–7.6 (m;1H;NH).

IR (film): 3310 (NH,OH), 3095 (NH), 2950 (CH$_2$), 2870 (CH$_2$), 1645 (CO), 1560 (CO).

MS: 178 (M$^+$+1), 159 (M$^+$−H$_2$O), 100 (M$^+$−SCH$_2$CH$_2$OH).

EXAMPLE 2

N-acetyl-3-aminopropyl 2-hydroxyethyl sulfide 78.1 g (1.0 mol) of mercaptoethanol in 100 ml of chlorobenzene are added dropwise at 60° C. to 99.1 g (1.0 mol) of N-allylacetamide in 250 ml of chlorobenzene over a period of 2 hours, and the mixture is stirred for 10 hours with the addition of air. After the solvent has been distilled off, 175.8 g of N-acetyl-3-aminopropyl 2-hydroxyethyl sulfide having a purity of 95.5% are obtained, which corresponds to a yield of 94.7% of theory.

The spectroscopic data concerning the nuclear magnetic resonance, mass and infrared spectra are identical to those mentioned in Example 1.

EXAMPLE 3

N-acetyl-3-aminopropyl 2-hydroxyethyl sulfide 99.1 g (1.0 mol) of N-allylacetamide are added dropwise at 25° C. to 78.1 g (1.0 mol) of mercaptoethanol over a period of 1 hour with vigorous stirring and addition of air. Stirring at room temperature is continued for 7 hours to give 177.2 g of 3-acetylaminopropyl 2-hydroxyethyl sulfide having a purity of 95.7%, which corresponds to a yield of 95.7% of theory.

The spectroscopic data concerning the nuclear magnetic resonance, mass and infrared spectra are identical to those mentioned in Example 1.

EXAMPLE 4

N-formyl-3-aminopropyl 2-hydroxyethyl sulfide 78.1 g (1.0 mol) of mercaptoethanol are added dropwise at 25° C. to 85.1 g (1.0 mol) of N-allylformamide over a period of 1 hour with vigorous stirring and addition of air. Stirring at room temperature is continued for 5 hours to give 163.2 g of N-formyl-3-aminopropyl 2-hydroxyethyl sulfide having a purity of 95.6%, which corresponds to a yield of 95.6% of theory.

$^1$H-NMR (CDCl$_3$): δ=1.30–2.10 (m;2H;CH$_2$CH$_2$CH$_2$), 2.58, 2.68 (t, J=7Hz;4H;2 —CH$_2$S), 3.35 (pseudo q, J=7Hz;2H;CH$_2$NH), 3.72 (t, J=7Hz;2H;CH$_2$OH), 4.35 (s;1H;$\overline{OH}$), 7.1–7.7 (m;1H;NH), 8.05 (d, J=14Hz;O,2H;Z—CHO), 8.10 (d, J=2Hz;0,8H;E—CHO).

IR (film): 3310 ($\overline{NH,OH}$), 3080 (NH), 2940 (CH$_2$), 2880 (CH$_2$), 1670 (CO), 1540 (CO).

MS: 145 (M$^+$−H$_2$O), 86 (M$^+$−SCH$_2$CH$_2$OH).

EXAMPLE 5

N-valeroyl-3-aminopropyl 2-hydroxyethyl sulfide 78.1 g (1.0 mol) of mercaptoethanol are added dropwise at 25° C. to 142.1 g (1.0 mol) of N-allylvaleramide over a period of 2 hours with vigorous stirring and addition of air. Stirring at room temperature is continued for 7 hours to give 219.2 g of 3-valeroylaminopropyl 2-hydroxyethyl sulfide having a purity of 96.2%, which corresponds to a yield of 96.2% of theory. The melting point is 7° C.

$^1$H-NMR (CDCl$_3$): δ=0.70–2.30 (m;11H), 2.35, 2.62 (t, J=7Hz;4H;2 —CH$_2$S), 3.25 (pseudo q, J=7Hz;2[lacuna];CH$_2$NH), 3.70 (t, J=7Hz;2H;CH$_2$OH), 4.9 (s;1H;OH), 6.9–7.5 (m;1H;NH).

IR (film): 3300 (NH,OH), 3090 (NH), 2940 (CH$_2$), 2880 (CH$_2$), 1650 (CO), 1550 (CO).

MS: 219 (M$^+$), 201 (M$^+$−H$_2$O), 142 (M$^+$−SCH$_2$CH$_2$OH).

EXAMPLE 6

N-acetyl-3-aminopropyl 2-hydroxyethyl sulfide

An oxygen/nitrogen mixture (1:5) is introduced into a mixture of 99.1 g (1.0 mol) of N-allylacetamide and 78.1 g (1.0 mol) of mercaptoethanol at 25° C. with vigorous stirring. After 8 hours, the reaction is complete (GC). 173.4 g of N-acetyl-3-aminopropyl 2-hydroxyethyl sulfide are formed as a yellowish oil having a purity by GC of 95.6%, which corresponds to a yield of 93.5% of theory.

The spectroscopic data concerning the nuclear magnetic resonance and infrared spectra are identical to those mentioned in Example 1.

EXAMPLE 7

N-acetyl-3-aminopropyl 2-hydroxyethyl sulfide 78.1 g (1.0 mol) of mercaptoethanol are added dropwise at 80° C. to 99.1 g (1.0 mol) of N-allylacetamide over a period of 2 hours with the addition of air, and stirring is continued for 4 hours. 177.1 g of N-acetyl-3-aminopropyl 2-hydroxyethyl sulfide having a purity of 91.5% are obtained, which corresponds to a yield of 91.5% of theory.

The spectroscopic data concerning the nuclear magnetic resonance, mass and infrared spectra are identical to those mentioned in Example 1.

EXAMPLE 8

Comparative Example

A mixture of 99.1 g (1.0 mol) of N-allylacetamide and 78.1 g (1.0 mol) of mercaptoethanol is vigorously stirred at 25° C. under a nitrogen atmosphere. After 8 hours, no reaction product has been formed according to GC and the starting materials are present unchanged.

EXAMPLE 9

3-aminopropyl 2-hydroxyethyl sulfide

Comparative Example according to the procedure of Example 3, page 18 of DE 2,040,620

57.0 g (1.0 mol) of allylamine are added dropwise at 80°–90° C. over a period of 2 hours to 78.1 g (1.0 mol) of mercaptoethanol to which 0.5 g of azoisobutyronitrile has been added. Stirring at 80°–90° C. is then continued for 10 hours to give 126.8 g of 3-aminopropyl 2-hydroxyethyl sulfide having a purity of 60.4%, which corresponds to a yield of 56.6% of theory.

EXAMPLE 10

3-aminopropyl 2-hydroxyethyl sulfide

Comparative Example according to the procedure of Example 3, page 18 of DE 2,040,620, except that air was used as the free-radical initiator 78.1 g (1.0 mol) of mercaptoethanol and 57.0 g (1.0 mol) of allylamine are vigorously stirred at 60° C. to give 124.7 g of a reaction mixture which, by GC and GC-MS, comprises 12% of 3-aminopropyl 2-hydroxyethyl sulfide, 19% of bis(2-hydroxyethyl) sulfide and unconverted starting materials.

EXAMPLE 11

N-(4-nitrobenzoyl)-3-aminopropyl 2-hydroxyethyl sulfide

Comparative Example according to the procedure of Example 1, page 15, of DE 2,040,620

40 g (0.5 mol) of mercaptoethanol are added at 120°–140° C. to 103 g (0.5 mol) of 4-nitro-N-allylbenzamide in the melt to which 0.1 g of azoisobutyronitrile had been added. Stirring at this temperature is then continued for 5 hours to give 143 g of N-(4-nitrobenzoyl)-3-aminopropyl 2-hydroxyethyl sulfide having a purity of 78.3%, which corresponds to a yield of 78.3% of theory.

What is claimed is:

1. An N-acylaminoalkyl 2-hydroxyethyl sulfide of the formula $$R-CONH-(CH_2)_n-S-CH_2-CH_2-OH$$

in which R is a hydrogen atom or an unbranched or branched alkyl($C_1$–$C_4$) radical and n is an integer of 3 to 6.

2. The compound of the formula $$CH_3-CONH-CH_2-CH_2-CH_2-S-CH_2-CH_2-OH.$$

3. The compound of the formula $$HCO-NH-CH_2-CH_2-CH_2-S-CH_2-CH_2-OH.$$

4. The compound of the formula $$C_4H_9-CO-NH-CH_2-CH_2-CH_2-S-CH_2-CH_2-OH.$$

5. The compound of the formula $$C_3H_7-CONH-CH_2-CH_2-CH_2-S-CH_2-CH_2-OH.$$

* * * * *

UNITED STATES PATENT AND TRADEMARK OFFICE
CERTIFICATE OF CORRECTION

PATENT NO. : 5,278,341  
DATED : January 11, 1994  
INVENTOR(S) : Michael Meier, et al.

Page 1 of 2

It is certified that error appears in the above-indentified patent and that said Letters Patent is hereby corrected as shown below:

On the title page, item (56) should read:

References Cited

U.S. PATENT DOCUMENTS 3,278,526  10/1966  Louthan et al.............504/209  
3,849,576  11/1974  Kalopissis................424/330

FOREIGN PATENT DOCUMENTS 2447966  8/1980  France  
2040620  2/1972  Germany

UNITED STATES PATENT AND TRADEMARK OFFICE
CERTIFICATE OF CORRECTION

PATENT NO. : 5,278,341

DATED : January 11, 1994

INVENTOR(S) : Michael Meier, et al.

Page 2 of 2

It is certified that error appears in the above-indentified patent and that said Letters Patent is hereby corrected as shown below:

OTHER PUBLICATIONS

Kandror et al, Selective Inhibition of the Radical Addition of Thiols to Olefins..., CA 77 (23): 151194g, 1972.

Signed and Sealed this

Twentieth Day of September, 1994

Attest:

BRUCE LEHMAN

*Attesting Officer*

*Commissioner of Patents and Trademarks*